United States Patent [19]

ten Broeke

[11] 4,232,026

[45] Nov. 4, 1980

[54] DIAZADITWISTANES, AND PHARMACEUTICAL COMPOSITIONS FOR TREATING PAIN IN WARM BLOODED ANIMALS CONTAINING THEM

[75] Inventor: Jan ten Broeke, Somerset, N.J.

[73] Assignee: Merck & Co., Inc., Rahway, N.J.

[21] Appl. No.: 926,353

[22] Filed: Jul. 20, 1978

[51] Int. Cl.$^3$ .................... A61K 31/47; C07D 471/08
[52] U.S. Cl. ........................................ 424/258; 546/63
[58] Field of Search .......................... 424/258; 546/63

[56] References Cited

U.S. PATENT DOCUMENTS

| | | | |
|---|---|---|---|
| 3,793,329 | 2/1974 | Merz et al. | 546/74 |
| 3,914,233 | 10/1975 | Mohacsi et al. | 546/74 |
| 3,931,189 | 1/1976 | Langbein et al. | 546/39 |
| 4,033,968 | 7/1977 | ten Broeke et al. | 546/63 |

OTHER PUBLICATIONS

Noller, Chemistry of Organic Compounds, 3rd ed., W. B. Saunders Co., Philadelphia (1965), pp. 164, 236, 238–239.
Liberatore, et al., Tetrahedron Letters, no. 26, pp. 2381–2384 (1971).
Hirao, et al., J. Chem. Soc., Chem. Comm., pp. 691–692 (1974).
ten Broeke, et al., J. Org. Chem., vol. 41, pp. 3159–3163 (1976).
Fisher, et al., J. Med. Chem., vol. 20, pp. 63–66 (1977).
Cardillo, et al., Chemical Abstracts, vol. 71, 112538d (1969).
Thiele, Chemical Abstracts, vol. 76, 45914m (1972).
Brown, et al., Chemical Abstracts, vol. 82, 57536b (1975).
Fuson, "Reactions of Organic Compounds", John Wiley & Sons, Inc., New York (1964), p. 571.

*Primary Examiner*—Donald G. Daus
*Assistant Examiner*—D. Rivers
*Attorney, Agent, or Firm*—Mario A. Monaco; William H. Nicholson

[57] ABSTRACT

Certain 2- and/or 9- phenylalkyl-5,11-dimethyl-5,11-diazaditwistane compounds bind to opiate receptor sites and have central nervous system activities exemplified by analgesia.

7 Claims, No Drawings

DIAZADITWISTANES, AND PHARMACEUTICAL COMPOSITIONS FOR TREATING PAIN IN WARM BLOODED ANIMALS CONTAINING THEM

BACKGROUND OF THE INVENTION

This invention is concerned with a new class of diazaditwistanes characterized by having a phenylalkyl group attached to either or both of the 2- and 9- positions of the complex ring system. The novel compounds have opiate receptor binding capability by virtue of which they are analgesic and antidiarrheal agents.

The diazaditwistane structure is relatively new appearing in the patent litereature first in U.S. Pat. No. 4,033,968 which disclosed a small class of analgesic compounds with an alkanoyl group at both the 2- and 9- positions. Molecular model studies comparing these compounds with enkephalins, and some of their analogs suggested that closer structural similarities with the enkephalins would be realized with the novel compounds of this invention.

Thus there is provided by the present invention a new class of diazaditwistanes characterized by a phenylalkyl group at either or both of the 2- and 9- positions which bind to opiate receptor sites and have central nervous system activities exemplified by analgesia.

There is also provided by this invention processes for preparing the novel compounds; pharmaceutical compositions employing the novel compounds as active ingredients; and a method of treating pain with the novel compounds and compositions of this invention.

DETAILED DESCRIPTION OF THE INVENTION

The novel compounds of this invention have structural formula:

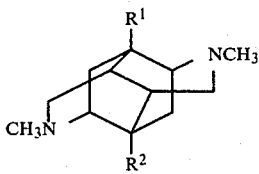

I or a pharmaceutically acceptable salt thereof, wherein $R^1$ is:

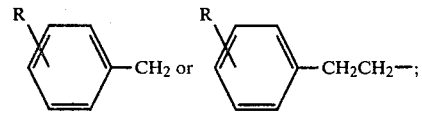

$R^2$ is:

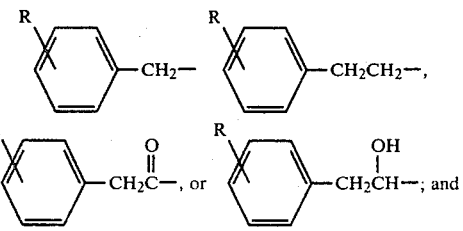

R is hydrogen or hydroxy.

It is preferred that $R^1$ and $R^2$ are both

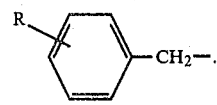

Another preferred embodiment is that wherein $R^1$ is 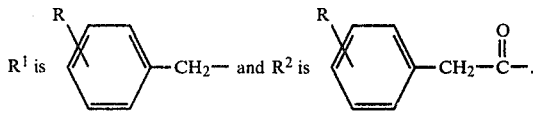 and $R^2$ is

This invention also contemplates the optical isomers of the novel compounds prepared by methods disclosed in U.S. Pat. No. 4,033,968 and mixtures of said isomers, including racemic mixtures.

The pharmaceutically acceptable salts of the novel analgesic compounds of this invention are acid addition salts prepared from inorganic or organic acids and include such as bitartrate, hydrobromide, camphorsulfonate (camsylate), citrate, ethane-1,2-disulfonate (edisylate), fumarate, hippurate, hydrochloride, maleate, mandelate, methanesulfonate (mesylate), methosulfate, 2-naphthalenesulfonate (napsylate), niacinate, oxalate, 4,4'-methylenebis (3-hydroxy-2-naphthoate) (pamoate), tartrate, carbamate, succinate, acetate, ethanesulfonate (esylate), lactate, palmitate, p-toluenesulfonate (tosylate), n-acetylglycinate, benzenesulfonate, hexanoate, p-chlorobenzenesulfonate, 3-cyclopentylpropionate, heptanoate, dodecylsulfate (estolate), o-(4-hydroxybenzoyl) benzoate, 2-hydroxyethanesulfonate (isethionate), 3-phenylpropionate, trimethylacetate (pivalate), t-butylacetate, or cyclamate.

A further embodiment of this invention comprises the novel intermediate compound of formula:

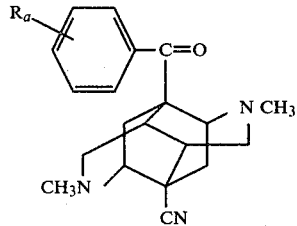

wherein $R_\alpha$ is —H or $C_{1-3}$alkyl, prepared by heating in a polar protic solvent at 100°–200° C., a compound of structure

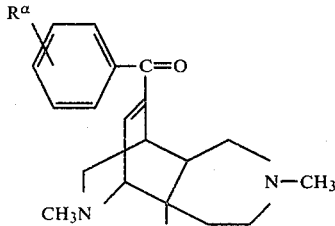

The novel compounds of this invention, are prepared by a variety of novel processes depending on the desired substitution.

Where the 2-, or 9- substituent is phenylacetyl the compound can be prepared by treating the corresponding 2-, or 9-carboxy, ester, nitrile, or amide with an organometallic reagent such as benzyl lithium, or benzyl magnesium halide, especially chloride in an inert solvent such as dialkyl ethers, 1,2-dimethoxyethane, tetrahydrofuran, dioxane or the like at temperatures from −40° C. to reflux for 1-24 hours.

Where the 2-, or 9- substituent is a 2-phenyl-1-hydroxyethyl the compound can be prepared by reduction of the preceding carbonyl compound with a borohydride such as sodium borohydride in a $C_{1-3}$ alkanol at 0° C. to reflux temperature for ½ to about 20 hours. Alternatively, the reduction can be accomplished catalytically with hydrogen in the presence of a noble metal catalyst such as platinum oxide in a $C_{1-3}$ alkanol preferably at room temperature at 1-3 atmospheres of pressure.

Where the substituent in the 2- or 9- substituent is phenalkyl, for example, benzyl or phenethyl the compound can be prepared by conversion of an α-hydroxy compound such as the preceding carbinol to a chlorocompound by treatment with thionyl chloride at about 50° C. to reflux temperature for 1 to about 5 hours followed by hydrogenolysis of the chloro group by treatment with an alkali metal and a lower carbinol, preferably lithium in t-butanol in an inert solvent such as tetrahydrofuran, dioxane dialkyl ether or the like at ambient temperature for about 2 hours to about 10 days.

An alternative route to the 2- or 9- phenalkyl substitution is by formation of the hydrazones of the corresponding 2- or 9- acyl compound and reduction under Wolff-Kishner conditions, for example in refluxing ethylene glycol in the presence of an alkali metal hydroxide.

A modification of the Wolff-Kishner is useful if sensitive groups such as methoxy is present in the intermediate. The process involves forming the semicarbazone of an acyl compound and treating that intermediate with potassium t-butoxide in xylene or toluene at reflux temperature for about 2 to about 60 hours.

Compounds carrying a phenolic hydroxyl group are usually prepared by treatment of the corresponding $C_{1-3}$ calkoxy compound with an excess of boron tribromide in a chlorinated hydrocarbon such as methylene chloride, tetrachloroethane or the like at about −100° to about −50° C.

Another embodiment of the invention, is a novel method of treating pain in a warm blooded animal (including man) by the administration of a compound of formula I at the rate of 0.1 to 50 mg/kg/day, preferably from 4-15 mg/kg/day in a suitable pharmaceutical formulation, which is another embodiment of this invention, adapted for oral, topical, parenteral, inhalation or rectal administration.

The pharmaceutical formulations for oral use may be in the form of tablets, troches, lozenges, aqueous or oral suspensions, dispersible powders and granules, emulsions, hard or soft capsules, syrups or elixirs and may be prepared according to methods known in the art for the manufacture of such compositions.

The pharmaceutical formulations for rectal use are in the form of suppositories prepared according to art recognized methods.

For topical use, creams, ointments, gels, solutions or suspensions are employed.

The pharmaceutical formulations for administration by injection are in the form of a sterile solution or suspension in a parenterally acceptable diluent or solvent.

The amount of active ingredient combined with the carrier materials of the pharmaceutical formulations to produce a single dosage form will vary depending on the mode of administration. For example, oral preparations should comprise from 5-500 mg, and preferably about 50-250 mg of active compound in combination with the carrier materials.

EXAMPLE 1

2,9-Bis-Benzyl-5,11-Dimethyl-5,11-Diazaditwistane

Step A: Preparation of 2,9-bis-benzimidoyl-5,11-dimethyl-5,11-diazaditwistane

A slurry of 24.24 g (100 mM) of 2,9-dicyano-5,11-dimethyl-5,11-diazaditwistane in 240 ml of dried tetrahydrofuran is treated under nitrogen with 100 ml of 2.3 Molar (230 mM) phenyl lithium in benzene. After standing at room temperature for 75 hours the tetrahydrofuran is evaporated and the resulting granular mass is crystallized with 500 ml ether and 75 ml water. After filtration, washed with ether and drying there is obtained 37.44 g (82.7%) of 2,9-bis-benzimidoyl-5,11-dimethyl-5,11-diazaditwistane trihydrate; m.p. 101°-107° C. with loss of ammonia.

Step B: Preparation of 2,9-bis-benzoyl-5,11-dimethyl-5,11-diazaditwistane

A solution of 20.0 g (44.2 mM) of 2,9-bis-benzimido-5,11-dimethyl-5,11-diazaditwistane in 150 ml of 1.5 N hydrochloric acid is aged at room temperature for 2 hours. After making alkaline the product is extracted into a total of 100 ml of methylene chloride, dried over $MgSO_4$, and obtained upon removal of the solvent as a crystal mass, 17.3 g (98.25%), m.p. 117°-124° C.

Step C: Preparation of 2,9-bis-benzyl-5,11-dimethyl-5,11-diazaditwistane

A solution of 2.00 g (5 mM) of 2,9-bis-benzoyl-5,11-dimethyl-5,11-diazaditwistane with 3.0 ml of hydrazine hydrate in 30 ml of absolute ethanol is aged at room temperature for 18 hours, at which time no more starting material is observed by tlc. The solution is concentrated under vacuum to give the crude 2,9-bis-benzhydrozono-5,11-dimethyl-5,11-diazaditwistane. After addition of 30 ml of ethylene glycol and 3 g of potassium hydroxide the reaction mixture is heated over a period of 1 hour to 180° C. under a small distillation head to remove water and excess hydrazine. After heating at 190° C. for a total of 22 hours the reaction mixture is cooled, treated with water and extracted with methylene chloride. The extract is dried over $MgSO_4$ and concentrated under vacuum to an amorphous mass which is chromatographed on silica gel to give the desired 2,9-bis-benzyl-5,11-dimethyl-5,11-diazaditwistane as a pale yellow oil which is converted to the dihydrochloride by dissolving in 50 ml of methylene chloride and introducing gaseous HCl, and concentration to a partly crystalline mass which on boiling with 30 ml of isopropanol affords 0.71 g of 2,9-bis-benzyl-5,11-dimethyl-5,11-diazaditwistane dihydrochloride. IR and NMR spectrum and tlc are in accord with the structure.

EXAMPLE 2

2-Phenylacetyl-9-(2-Phenylethyl)-5,11-Dimethyl-5,11-Diazaditwistane

A solution of 4.28 g (10 mM) of 2,9-bis-phenylacetyl-5,11-dimethyl-5,11-diazaditwistane and 6 ml of hydrazine hydrate in 60 ml of absolute ethanol is allowed to react at room temperature for 24 hours, at which time essentially no more starting material is observable by tlc. After addition of ethylene glycol and 6 g of potassium hydroxide pellets the solution is heated slowly over a period of 2 hours to 185° C. while 70 ml of ethanol, water and excess hydrazine are distilled off. After 70 hours at 185° C., 100 ml of water is added and the reaction mixture is extracted with a total of 70 ml of methylene chloride, which is dried over MgSO$_4$ and concentrated to 3.69 g of residue. A 2.5 g part of this mixture is dissolved in 5 ml of 2.5 N hydrochloric acid, filtered quickly from a small amount of insoluble contamination and allowed to crystallize. The dihydrochloride of 2,9-bis-(2-phenylethyl)-5,11-dimethyl-5,11-diazaditwistane is filtered off and washed with a total of 6 ml of 2.5 N hydrochloric acid. The HCl filtrate is allowed to sit at room temperature for 3 days to complete the hydrolysis. The reaction mixture is made alkaline with 2.5 N sodium hydroxide and extracted with methylene chloride to give 1.14 g of crude 2-phenylacetyl-9-(2-phenylethyl)-5,11-dimethyl-5,11-diazaditwistane. Chromatography through 200 g of silica gel yields 480 mg of nearly pure material which is rechromatographed through 200 g of silica gel to yield 254 mg of a yellow oil which is treated in methylene chloride with gaseous hydrochloric acid to give a hygroscopic dihydrochloride salt which equilibrates to a hemiheptahydrate. NMR, IR and Mass spectrum are in accord with the structure. Anal. for $C_{28}H_{34}N_2O.2HCl.3.5\ H_2O$: Calc. C, 61.08; H, 7.84; N, 5.08; Cl, 12.87; Found: C, 60.73; H, 7.49; N, 4.93; Cl, 12.91.

EXAMPLE 3

2-Benzyl-9-Phenylacetyl-5,11-Dimethyl-5,11-Diazaditwistane

Step A: Preparation of 11-benzoyl-7-cyano-4,9-dimethyl-4,9-diazatricyclo[6.2.2.0$^{2,7}$]dodec-11-ene A solution of 12.12 g (50 mM) of 7,11-dicyano-4,9-dimethyl-4,9-diazatricyclo[6.2.2.0$^{2,7}$]dodec-11-ene in 150 ml of dried THF is cooled in dry ice-acetone and treated with 26 ml of 1.67 molar (43.5 mM) phenyl lithium in benzene over a 15 minute period. The reaction mixture is allowed to stir at room temperature overnight and then treated with 50 ml of 2.5 N hydrochloric acid. The layers are separated and the tetrahydrofuranbenzene layer is extracted with 20 ml of 1 N hydrochloric acid. The combined product-containing hydrochloric acid layers are washed with methylene chloride and allowed to sit at room temperature for 2 hours. After making alkaline with 5 ml of 50% sodium hydroxide solution the product is extracted into a total of 125 ml of methylene chloride which after drying over MgSO$_4$, and concentration yields 11.35 g of a crude product. By chromatography over silica gel 11-benzoyl-7-cyano-4,9-dimethyl-4,9-diazatricyclo[6.2.2.0$^{2,7}$]dodec-11-ene is isolated analytically pure in an overall yield of 16%, m.p. 120°–139° C., NMR and IR spectrum are in accord with the structure.

Step B: Preparation of 2-benzoyl-9-cyano-5,11-dimethyl-5,11-diazaditwistane

A solution of 1.35 g of the crude 11-benzoyl-7-cyano-4,9-dimethyl-4,9-diazatricyclo[6.2.2.0$^{2,7}$]dodec-11-ene in 2.5 ml of acetic acid and 25 ml of water is refluxed for 2½ hours. The reaction mixture is extracted with a total of 60 ml of methylene chloride and the extract is washed with 10 ml of 1 N sodium hydroxide, dried over MgSO$_4$ and concentrated under vacuum to yield 0.34 g, m.p. 76°–122° C., NMR and IR spectrum and tlc are in accord with the structure.

Step C: Preparation of 2-benzhydrazono-9-cyano-5,11-dimethyl-5,11-diazaditwistane A solution of 1.00 g (3.12 mM) of 2-benzoyl-9-cyano-5,11-dimethyl-5,11-diazaditwistane in 15 ml of absolute ethanol with 1.5 ml of hydrazine hydrate is aged at room temperature for 20 hours and then concentrated under vacuum to a crystal mass of 1.84 g. A sample is washed with ethanol to yield material m.p. 167°–178° C., NMR and IR spectrum are in accord with the structure.

Step D: Preparation of 2-benzyl-9-carboxy-5,11-dimethyl-5,11-diazaditwistane

A mixture of 1.84 g of the hydrazone from Step D, 1.0 ml of hydrazine hydrate, 1.5 g of potassium hydroxide pellets and 15 ml of ethylene glycol is heated slowly to 190° C., maintained at 190° C. for 90 hours, cooled and treated with 40 ml water. Potassium ions are removed by ion exchange over 75 ml of a cation exchange resin on the ammonium cycle and the ethylene glycol is removed by absorbing the product onto the same resin on the H$^+$ cycle. The product is eluted with dilute ammonia. After removal of the solvent and slurrying of the residue with methanol there is obtained 0.35 g of 2-benzyl-9-carboxy-5,11-dimethyl-5,11-diazaditwistane, m.p. >275° C. NMR and IR spectrum are in accord with the structure.

Step E: Preparation of 2-benzyl-9-phenylacetyl-5,11-dimethyl-5,11-diazaditwistane A slurry of 3.26 g (10 mM) of 2-benzyl-9-carboxy-5,11-dimethyl-5,11-diazaditwistane in 35 ml of dried tetrahydrofuran with 20 mM of anhydrous magnesium bromide, pregenerated from 0.48 g (20 mM) of magnesium and 3.74 g (20 mM) of dibromoethane, is treated with 12 ml of 2.1 Molar benzyl magnesium chloride in tetrahydrofuran and refluxed for 4 hours. The reaction mixture is cooled in an ice bath and treated below 15° C. with a solution of 5 g of ammonium chloride in 25 ml water. The layers are separated and the tetrahydrofuran layer is washed with a solution of 5 g of ammonium chloride in 25 ml water, and the aqueous washes are backwashed with 25 ml of ether. To hydrolyze the imine and to remove neutral by-products the organic layers are extracted with 10 ml of 2.5 N hydrochloric acid and the acidic layer is washed with 20 ml ether. After 1 hour at room temperature 11 ml of 2.5 N sodium hydroxide is added to the HCl solution, and the product is extracted into a total of 55 ml of methylene chloride which is dried and concentrated to dryness to give 2-benzyl-9-phenyacetyl-5,11-dimethyl-5,11-diazaditwistane.

EXAMPLE 4

2-Benzyl-9-(4-Hydroxyphenyl)acetyl-5,11-Dimethyl-5,11-Diazaditwistane

Step A: Preparation of 2-benzyl-9-(4-methoxyphenyl)acetyl-5,11-dimethyl-5,11-diazaditwistane Employing the procedure described in Example 3, Step E, but substituting for the benzyl magnesium chloride used therein an equimolecular amount of 4-methoxybenzylmagnesium chloride, there is prepared 2-benzyl-9-(4-methoxyphenyl)acetyl-5,11-dimethyl-5,11-diazaditwistane.

Similarly prepared are 2-benzyl-9-(3-methoxyphenyl)acetyl-5,11-dimethyl-5,11-diazaditwistane; and 2-benzyl-9-(2-methoxyphenyl) acetyl-5,11-dimethyl-5,11-diazaditwistane.

Step B: Preparation of 2-benzyl-9-(4-hydroxyphenyl)acetyl-5,11-dimethyl-5,11-diazaditwistane A solution of 1.29 g (4 mM) of 2-benzyl-9-(4-methoxyphenyl)acetyl-5,11-dimethyl-5,11-diazaditwistane in 120 ml of methylene chloride is cooled in a dry ice-acetone bath to −70° C. under a nitrogen atmosphere, and treated over a 50 minute period with 8 ml of 2 Molar (16 mM) boron tribromide in methylene chloride. The reaction mixture is allowed to stir with dry ice-acetone cooling for 1 hour and with ice cooling for 2 hours and then quenched with 10 ml of anhydrous ethyl ether to destroy the excess reagent. The solvent is removed by evaporation under vacuum, the residue is extracted with methylene chloride containing 10% by volume of methanol and the product is isolated by chromatography over 100 g silica gel, pretreated with ammonia vapor, using a gradient of methylene chloride to methylene chloride with 25% by volume of methanol.

Similarly prepared are 2-benzyl-9-(3-hydroxyphenyl)acetyl-5,11-dimethyl-5,11-diazaditwistane, and 2-benzyl-9-(2-hydroxyphenyl)acetyl-5,11-dimethyl-5,11-diazaditwistane.

EXAMPLE 5

2-Benzyl-9-(2-phenyl-1-hydroxyethyl)-5,11-dimethyl-5,11-diazaditwistane

A reaction mixture consisting of 0.83 g (2 mM) of 2-benzyl-9-phenylacetyl-5,11-dimethyl-5,11-diazaditwistane and 0.076 g (2 mM) of sodium borohydride in 8 ml of isopropanol is refluxed for 2 hours. A trace of inorganic insolubles is removed by filtration and the organic solvent is removed under vacuum. The residue is extracted with a total of 50 ml of methylene chloride and on evaporation of the volatiles there is obtained 2-benzyl-9-(2-phenyl-1-hydroxyethyl)-5,11-dimethyl-5,11-diazaditwistane.

Similarly prepared are:
2-benzyl-9-[2-(4-hydroxyphenyl)-1-hydroxyethyl]5,11-dimethyl-5,11-diazaditwistane;
2-benzyl-9-[2-(3-hydroxyphenyl)-1-hydroxyethyl]5,11-dimethyl-5,11-diazaditwistane; and
2-benzyl-9-[2-(2-hydroxyphenyl)-1-hydroxyethyl]-5,11-dimethyl-5,11-diazaditwistane.

EXAMPLE 6

2-Benzyl-9-(4-Hydroxyphenethyl)-5,11-Dimethyl-5,11-Diazaditwistane

Step A: Preparation of 2-benzyl-9-[2-(4-methoxyphenyl)-1-hydroxyethyl]-5,11-dimethyl-5,11-diazaditwistane Using the procedure as described in Example 5 but employing the 4-methoxyphenylacetyl compound as starting material there is produced 2-benzyl-9-[2-(4-methoxyphenyl)-1-hydroxyethyl]5,11-dimethyl-5,11-diazaditwistane.

Similarly prepared are:
2-benzyl-9-[2-(3-methoxyphenyl)-1-hydroxyethyl]-5,11-dimethyl-5,11-diazaditwistane; and
2-benzyl-9-[2-(2-methoxyphenyl)-1-hydroxyethyl]-5,11-dimethyl-5,11-diazaditwistane.

Step B: Preparation of 2-benzyl-9-[2-(4-methoxyphenyl)-1-chloroethyl]-5,11-dimethyl-5,11-diazaditwistane A solution of 5 mM of the carbinol from Step A in 50 ml of thionyl chloride is refluxed for 2 hours and concentrated to dryness in vacuo. The residue is distributed between methylene chloride and sodium bicarbonate solution. The organic layer is separated, dried over MgSO$_4$ and concentrated to dryness in vacuo. The residue is used directly in the next step.

Similarly prepared are:
2-benzyl-9-[2-(3-methoxyphenyl)-1-chloroethyl]-5,11-dimethyl-5,11-diazaditwistane;
2-benzyl-9-[2-(2-methoxyphenyl)-1-chloroethyl]-5,11-dimethyl-5,11-diazaditwistane; and
2-benzyl-9-(2-phenyl-1-chloroethyl)-5,11-dimethyl-5,11-diazaditwistane.

Step C: Preparation of 2-benzyl-9-(4-methoxyphenethyl)-5,11-dimethyl-5,11-diazaditwistane A mixture of 15 mM of product from Step B and 1.04 g (150 mA) of thin lithium leaflets in 60 ml of dried tetrahydrofuran is treated five times with 3 ml portions of t-butanol at hourly intervals, allowed to stir at ambient temperature for 72 hours, and treated with 50 ml of saturated NaCl solution. The tetrahydrofuran layer is separated, dried over MgSO$_4$ and concentrated under vacuum to a mass which is extracted with ether. The ether soluble oil is dissolved in 75 ml of ethanol and treated with hydrogen on a shaker in the presence of 1.0 g 5% Pd on Carbon for 90 hours. The catalyst is removed by filtration and the solvent is removed by concentration to leave a residue which is dissolved in 25 ml of 1 N hydrochloric acid, filtered from a little insoluble oil and treated with 3 ml of concentrated hydrochloric acid. This is concentrated to dryness and the residue of the dihydrochloride is converted to the free base by treatment with sodium bicarbonate solution, extraction into methylene chloride and concentration to dryness.

Similarly prepared are:
2-benzyl-9-(3-methoxyphenethyl)-5,11-dimethyl-5,11-diazaditwistane;
2-benzyl-9-(2-methoxyphenethyl)-5,11-dimethyl-5,11-diazaditwistane; and
2-benzyl-9-phenyethyl-5,11-dimethyl-5,11-diazaditwistane.

Step D: Preparation of 2-benzyl-9-(4-hydroxyphenethyl)-5,11-dimethyl-5,11-diazaditwistane Treatment of the product from Step C with boron tribromide as described in Example 4, Step C provides 2-benzyl-9-(4-hydroxyphenethyl)-5,11-dimethyl-5,11-diazaditwistane.

Similarly are prepared:
2-benzyl-9-(3-hydroxyphenethyl)-5,11-dimethyl-5,11-diazaditwistane; and
2-benzyl-9-(2-hydroxyphenethyl)-5,11-dimethyl-5,11-diazaditwistane.

EXAMPLE 7

2-Benzyl-9-(4-Hydroxybenzyl)-5,11-Dimethyl-5,11-Diazaditwistane

Step A: Preparation of 2-benzyl-9-(4-methoxybenzoyl)-5,11-dimethyl-5,11-diazaditwistane Treatment of 2-benzyl-9-carboxy-5,11-dimethyl-5,11-diazaditwistane with 4-methoxyphenyllithium in a procedure substantially as described in Example 3, Step E provides 2-benzyl-9-(4-methoxybenzoyl)-5,11-dimethyl-5,11-diazaditwistane.

Similarly prepared are:
2-benzyl-9-(3-methoxybenzoyl)-5,11-dimethyl-5,11-diazaditwistane; and
2-benzyl-9-(2-methoxybenzoyl)-5,11-dimethyl-5,11-diazaditwistane.

Employing the procedures substantially as described in Example 6, Steps A and B, but substituting for the phenylacetyl starting materials used therein, the corresponding benzoyl compounds there are produced in sequence:

Step B: (Procedure of Example 6, Step A)

2-benzyl-9-(4-methoxy-α-hydroxybenzyl)-5,11-dimethyl-5,11-diazaditwistane.

Step C: (Procedure of Example 6, Step B)

2-benzyl-9-(4-methoxy-α-chlorobenzyl)-5,11-dimethyl-5,11-diazaditwistane.

Step D: Preparation of 2-benzyl-9-(4-methoxybenzyl)-5,11-dimethyl-5,11-diazaditwistane A mixture of 6.8 mM of the α-chlorobenzyl compound, 0.5 g of lithium hammered into thin leaflets, and 3.0 ml of t-butanol in 30 ml of dried tetrahydrofuran is stirred at room temperature for 6 days, then quenched with 100 g of ice and extracted with a total of 60 ml of methylene chloride. The organic extracts are concentrated under vacuum to an oil which is dissolved in 20 ml of methylene chloride and treated with gaseous hydrochloric acid to give a precipitate which is filtered off, washed with ether and dried to yield 2-benzyl-9-(4-methoxybenzyl)-5,11-dimethyl-5,11-diazaditwistane dihydrochloride.

Step E: Preparation of 2-benzyl-9-(4-hydroxybenzyl)-5,11-dimethyl-5,11-diazaditwistane Treatment of the 4-methoxy compound with boron tribromide as described in Example 4, Step C, provides 2-benzyl-9-(4-hydroxybenzyl)-5,11-dimethyl-5,11-diazaditwistane.

Employing the procedures substantially as described in Example 7, Steps A through E, there are prepared:
2-benzyl-9-(3-hydroxybenzyl)-5,11-dimethyl-5,11-diazaditwistane; and
2-benzyl-9-(2-hydroxybenzyl)-5,11-dimethyl-5,11-diazaditwistane.

EXAMPLE 8

2-Benzyl-9-(4-Hydroxybenzyl)-5,11-Dimethyl-5,11-Diazaditwistane

Step A: Preparation of 2-benzoyl-9-(4-methoxybenzoyl)-5,11-dimethyl-5,11-diazaditwistane and 2,9-bis(4-methoxybenzoyl)-5,11-dimethyl-5,11-diazaditwistane A warm solution of 29.0 g (120 mM) of 2,9-dicyano-5,11-dimethyl-5,11-diazaditwistane in 300 ml of dried tetrahydrofuran is treated with a solution of 4-methoxyphenyl lithium prepared from 28.06 g 4-bromoanisole in 280 ml of anhydrous ether with 75 ml of 1.7 Molar (127.5 mM) n-butyl lithium in hexane. After 1¾ hours at room temperature 100 ml 1.6 Molar (160 mM) phenyl lithium is added and the reaction mixture is allowed to stir for 20 hours and is then quenched with 300 ml of ice and 70 ml of concentrated hydrochloric acid. The layers are separated and washed and backwashed. After 1 hour at room temperature the acid layer is basified with 45 ml of 50% sodium hydroxide and extracted with a total of 200 ml of methylene chloride. The organic layer is dried over $MgSO_4$ and concentrated under vacuum to a crystal mass, which is washed with a total of 150 ml of acetone to yield 21.4 g, m.p. 165°–190° C. Mass spectral analysis showed a mixture of m/e 430 for 2-benzoyl-9-(4-methoxybenzoyl-5,11-dimethyl-5,11-diazaditwistane, and m/e 460 for 2,9-bis-(4-methoxybenzoyl)-5,11-dimethyl-5,11-diazaditwistane and no m/e 400 for 2,9-bis-benzoyl-5,11-dimethyl-5,11-diazaditwistane.

Step B: Preparation of 2-α-hydroxybenzyl-9-(4-methoxy-α-hydroxybenzyl)-5,11-dimethyl-5,11-diazaditwistane and 2,9-bis-(4-methoxy-α-hydroxybenzyl)-5,11-dimethyl-5,11-diazaditwistane The crude 21.3 g from Step A is treated with 5.0 g of sodium borohydride in 210 ml of isopropanol at reflux for 3½ hours. The reaction mixture is treated with 250 ml of water and 200 ml of methylene chloride and the layers are separated. After washing with water and drying over $MgSO_4$, the organic layer is concentrated under vacuum to yield 23.7 g, of product. The IR spectrum shows strong OH absorption and the absence of any carbonyl absorption.

Step C: Preparation of 2-α-chlorobenzyl-9-(4-methoxy-α-chlorobenzyl)-5,11-dimethyl-5,11-diazaditwistane and 2,9-bis-(4-methoxy-α-chlorobenzyl)-5,11-dimethyl-5,11-diazaditwistane The total crude 23.7 g from Step B is chilled with dry ice-acetone and treated with 115 ml of thionyl chloride and refluxed for 3 hours. After removal of the thionyl chloride under vacuum the dark residue is dissolved in 400 ml of methylene chloride and added to 500 ml of saturated sodium bicarbonate solution. The methylene chloride layer is washed with a total of 200 ml of saturated sodium bicarbonate, dried over $MgSO_4$ and concentrated under vacuum to yield 23.4 g of product. The IR spectrum shows no more OH absorption.

Step D: Preparation of 2-benzyl-9-(4-methoxybenzyl)-5,11-dimethyl-5,11-diazaditwistane and 2,9-bis-(4-methoxybenzyl)-5,11-dimethyl-5,11-diazaditwistane The total crude from Step C in 200 ml of dried tetrahydrofuran and 30 ml of t-butanol is treated over a period of 1 hour with a total of 5.0 g lithium which had been hammered into many thin leaflets. After stirring for an additional 3½ hours at room temperature the reaction mixture is decanted from unused lithium and the organic layer is washed with 300 ml of ice water and with 200 ml of brine and concentrated under vacuum. The residue is dissolved in 150 ml of methylene chloride, dried over MgSO₄ and concentrated to a residue weighing 17.48 g. Mass spectral analysis shows a mixture of m/e 403 for 2-benzyl-9-(4-methoxybenzyl)-5,11-dimethyl-5,11-diazaditwistane and m/e 433 for 2,9-bis-(4-methoxybenzyl)-5,11-dimethyl-5,11-diazaditwistane.

Step E: Preparation of 2-benzyl-9-(4-hydroxybenzyl)-5,11-dimethyl-5,11-diazaditwistane The total crude from Step D is dissolved in 200 ml of methylene chloride, cooled in a dry ice-acetone bath under nitrogen and treated with 62.5 ml of 2.0 molar boron tribromide in methylene chloride over a 1 hour period. The reaction mixture is allowed to stir at −70° C. for 1 hour and at 0° C. for 2 hours and then quenched with 100 ml of ether at 0°–5° C. over a 15 minute period. After stirring at 0.5° C. for 1 hour the slurry is filtered and washed with a total of 150 ml of ether. The insolubles are treated with 100 ml of 15% potassium hydroxide and 100 ml of methylene chloride and stirred for 1 hour. After separation of the layers and introduction of $CO_2$ into the caustic layer there is obtained a crude oil which after drying weighs 7.8 g. After chromatography through silica gel an oil is obtained with the correct mass by mass spectral analysis m/e 388, single spot by tlc, and IR and NMR spectra in accord with the structure. After conversion of the free base to the hydrochloride there is obtained 2-benzyl-9-(4-hydroxybenzyl)-5,11-dimethyl-5,11-diazaditwistane dihydrochloride hydrate.

Anal. for $C_{26}H_{32}N_2O·2HCl·H_2O$; Calc: C, 65.13; H, 7.57; N, 5.84; Cl, 14.79; Found: C, 65.11; H, 7.70; N, 5.65; Cl, 14.40.

Employing the procedures described in Examples 1 through 7 additional compounds that can be prepared are as shown in the following table:

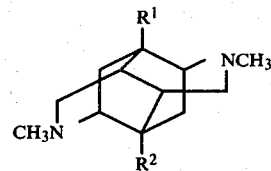

| R¹ | R² |
|---|---|
| 2-hydroxybenzyl- | phenacetyl |
| 3-hydroxybenzyl- | phenacetyl |
| 4-hydroxybenzyl- | phenacetyl |
| phenethyl | 2-hydroxybenzyl- |
| phenethyl | 3-hydroxybenzyl- |

-continued

| R¹ | R² |
|---|---|
| phenethyl | 4-hydroxybenzyl- |
| phenethyl | 2-hydroxyphenacetyl- |
| phenethyl | 3-hydroxyphenacetyl- |
| phenethyl | 4-hydroxyphenacetyl- |
| phenethyl | 2-(4-hydroxyphenyl)-1-hydroxyethyl- |
| phenethyl | 2-(3-hydroxyphenyl)-1-hydroxyethyl- |
| phenethyl | 2-(2-hydroxyphenyl)-1-hydroxyethyl- |
| 4-hydroxyphenethyl | phenacetyl |
| 3-hydroxyphenethyl | phenacetyl |
| 2-hydroxyphenethyl | phenacetyl |
| 4-hydroxyphenethyl | 2-phenyl-1-hydroxyethyl |
| 3-hydroxyphenethyl | 2-phenyl-1-hydroxyethyl |
| 2-hydroxyphenethyl | 2-phenyl-1-hydroxyethyl |
| 4-hydroxybenzyl | 2-phenyl-1-hydroxyethyl |
| 3-hydroxybenzyl | 2-phenyl-1-hydroxyethyl |
| 2-hydroxybenzyl | 2-phenyl-1-hydroxyethyl |

What is claimed is:

1. A compound of structural formula:

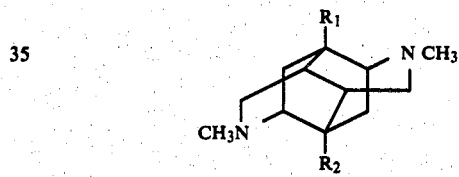

or a pharmaceutically acceptable salt thereof wherein:

R¹ is 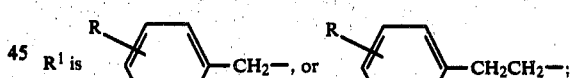

R² is 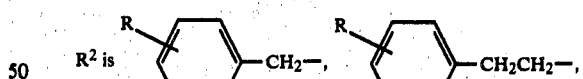

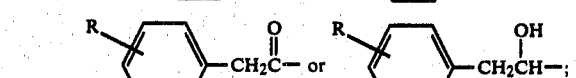

and

R is —H, or —OH.

2. The compound of claim 1, wherein R¹ and R² are both

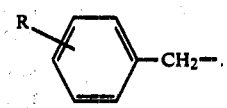

3. The compound of claim 1, wherein R¹ is

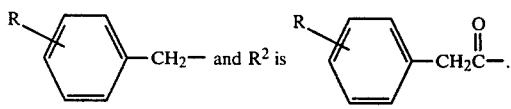 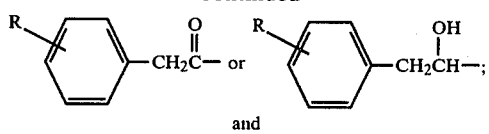

R is —H or —OH.

4. A pharmaceutical composition for treating pain in a warm blooded animal comprising a pharmaceutical carrier and an effective amount of a compound of formula:

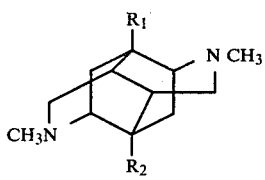

or a pharmaceutically acceptable salt thereof, wherein:

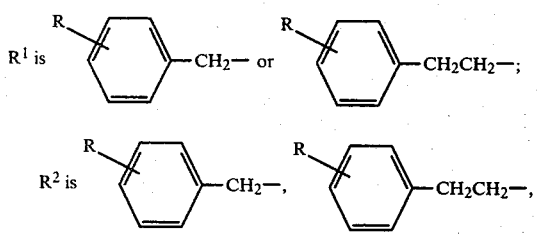

5. A compound of structural formula:

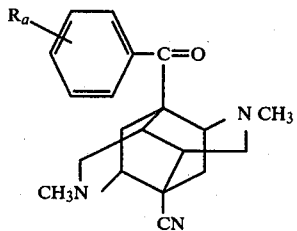

wherein $R_a =$ —H or $C_{1-3}$ alkoxy.

6. The pharmaceutical composition of claim 4, wherein $R^1$ and $R^2$ are both

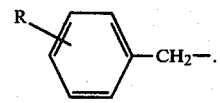

7. The pharmaceutical composition of claim 4, wherein $R^1$ is

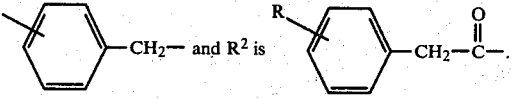

* * * * *